United States Patent
Phung et al.

(10) Patent No.: US 6,770,062 B2
(45) Date of Patent: Aug. 3, 2004

(54) AUTOMATIC HIGH NEGATIVE PRESSURE RELIEF VALVE AND CHEST DRAINAGE UNITS USING SAME

(76) Inventors: Trinh D. Phung, 63 Bambury La., Attleboro, MA (US) 02703; Daniel A. Boardman, 56 Cedar Cove Rd., Swansea, MA (US) 02777

( * ) Notice: Subject to any disclaimer, the term of this patent is extended or adjusted under 35 U.S.C. 154(b) by 69 days.

(21) Appl. No.: 10/213,785

(22) Filed: Aug. 7, 2002

(65) Prior Publication Data

US 2004/0030322 A1 Feb. 12, 2004

(51) Int. Cl.$^7$ .................................................. A61M 1/00
(52) U.S. Cl. ...................... 604/320; 137/458; 137/116.3
(58) Field of Search .................................. 604/317, 319, 604/320; 137/116.3, 458, 492.5

(56) References Cited

U.S. PATENT DOCUMENTS

| | | |
|---|---|---|
| 3,550,647 A | 12/1970 | Beach |
| 4,372,336 A | 2/1983 | Cornell et al. |
| 4,519,796 A | 5/1985 | Russo |
| 4,540,413 A | 9/1985 | Russo |
| 4,550,749 A | 11/1985 | Krikorian |
| 4,605,400 A | 8/1986 | Kurtz et al. |
| 4,768,542 A | 9/1988 | Morris |
| 5,053,026 A * | 10/1991 | Andersen et al. ............ 604/319 |
| 5,174,328 A * | 12/1992 | Maruyama et al. ......... 137/491 |
| 5,634,494 A | 6/1997 | Martens |
| 5,871,027 A | 2/1999 | Shimizu et al. |
| 5,989,234 A | 11/1999 | Valerio et al. |
| 6,024,120 A | 2/2000 | Yam et al. |
| 6,024,731 A * | 2/2000 | Seddon et al. .............. 604/317 |
| 6,358,218 B1 | 3/2002 | Want et al. |
| 6,368,311 B1 * | 4/2002 | Valerio et al. .............. 604/322 |

OTHER PUBLICATIONS

Patricia Carrol RN RRT BS, "Understanding Chest Drainage", Copyright 1995 Deknatel, Inc., July 1995.

* cited by examiner

Primary Examiner—John J. Calvert
Assistant Examiner—Michael G. Bogart
(74) Attorney, Agent, or Firm—Dechert, LLP; John W. Ryan

(57) ABSTRACT

Featured is an automatic high-negative pressure relief valve and its use in combination with an apparatus for draining fluid from a body. In broad terms the negative pressure relief valve includes a biasing mechanism, a moveable member acted upon by the biasing mechanism and a seating surface. When the pressure within a chamber, in which a portion of the relief valve is in fluid communication with, is less than a predetermined negative pressure, the moveable member is moved by the biasing mechanism to sealing engage the seating surface and when the pressure is at or above the predetermined value, the restoring force of the biasing mechanism is overcome and the moveable member moves away from the seating surface. In an exemplary embodiment, the biasing mechanism is a spring, diaphragm or wave washer.

21 Claims, 11 Drawing Sheets

AUTOMATIC HIGH NEGATIVE PRESSURE RELIEF VALVE AND CHEST DRAINAGE UNITS USING SAME

FIELD OF INVENTION

The present invention relates to fluid flow/pressure control and more particularly to methods, apparatuses and devices concerning the automatic relief of an excess negative pressure condition within an apparatus, vessel, medical device or other fluid container.

BACKGROUND OF THE INVENTION

As is known to those skilled in the medical arts, a number of situations can arise in which it is medical necessary to provide a drain from the pleural cavity. In these cases the pleural cavity is disrupted because of, for example, a blunt trauma injury (e.g., knife wound, gunshot wound, severe automobile accidents) and intentional chest trauma, for examples such as that resulting from thoracic surgical procedures requiring the drainage of air and/or fluid from collecting in the pleural cavity. Other pleural abnormalities include pleural effusion and empyema.

In addition, after heart surgery there is the possibility of the accumulation of blood and clots, for example, in the mediastinum, specifically in the pericardial sac, which can be life threatening. Thus, a drain can be provided for mediastinal drainage to minimize the risk of cardiac tamponade.

Initially and traditionally, such chest drainage was accomplished using what has been commonly referred to as a three-bottle chest drainage system. Since then, a number of devices have been developed to mimic the three-bottle system, which devices are sometimes referred to simply as chest drainage units. Such chest drainage units include a mechanism for collecting the liquid effluent from the patient, a patient seal that acts as a one-way valve so as to allow gaseous effluent to leave the pleural cavity but prevents a gas such as air from returning to the pleural cavity and a mechanism for limiting or controlling the amount of suction that can be applied to the pleural cavity by the chest drainage unit. A line(s) also is typically provided to connect the chest drainage unit to the pleural cavity and/or the mediastinum so that fluids can be withdrawn therefrom and collected in the chest drainage unit. In addition, another portion of the chest drainage unit is connected to a negative pressure source or vacuum/suction source, so as to cause the fluid or liquid effluent to flow to the drainage device and, in the case of the pleural cavity also maintaining a negative pressure in the pleural cavity so as not to compromise the full expansion of the lung.

It is possible to develop high or excess negative pressure conditions within such chest drainage units that must be relieved so as to avoid or minimize the risk of damage to tissue surrounding the drainage tube within the patient's body. Thus, specific measures or mechanisms are put into place so that such high or excess negative pressure conditions (i.e., a more negative pressure condition) can be removed and so that normal negative operational conditions can be re-established within the chest drainage unit.

Such high negative pressure conditions can result from a number of circumstances including, for example, patient coughing or medical personnel milking or stripping of the drainage tubing so as to cause any clots or the like to move towards the chest drainage unit. Milking is a term that is generally used to describe gentle kneading of short sections of the tubing so as to cause momentary bursts of suction within the tubing. Stripping is a much more vigorous procedure during which long lengths of the tubing are compressed and released. Stripping can cause dangerously high negative pressures.

Initially, one form of protection from high or excess negative pressure condition was a manually actuated valve whereby the medical personnel would depress or push a button of the manually actuated valve so as to allow external air to be introduced into the chest drainage unit, thereby alleviating the high negative pressure condition. For this form of protection to work, however, the medical personnel must first observe the patient and determine that a high negative pressure condition exists before they would actuate the manual valve. Thus, it may take some time after the onset of the high or excess negative pressure condition before such a condition is detected by the medical personnel and rectified by manual actuation of the relief valve.

Some recent chest drainage units, particularly those units that embody a dry suction type of control mechanism, for example that shown in U.S. Pat. No. 5,989,234, have included an automatic high-pressure negative pressure relief valve alone or in combination with a manually actuated relief valve. The automatic pressure relief valve is configured so it automatically opens and closes responsive to the negative pressure conditions within the chest drainage unit. Further, such an automatic relief valve typically is configured to open when a predetermined negative pressure condition or an even more negative condition is established within the collection chamber or section of the chest drainage unit, which pressure condition is in excess (i.e., more negative) of any of the normal operating suction or negative pressure conditions that can be developed in the collection chamber or section. For example, in some chest drainage units with a dry suction control regulation device designed to maintain suction pressures up to and including −40 cm of water, the set point for the automatic negative pressure relief valve is about −50 cm of water.

One such automatic high or excessive negative pressure relief valve is the adjustable check valve found in U.S. Pat. No. 4,550,749. Material properties of the resilient valve element of this pressure relief valve, such as the rigidity of the material, dictates at what pressure and where the resilient valve element will reseal. Consequently, this valve does not close as accurately as is desired. In addition, it has been observed that the pressure differential for closure varies from valve to valve. This failure to close accurately necessarily means that more air is being admitted into the chest drainage unit than is needed to overcome the high negative pressure condition. As such, the excess air needs to be withdrawn from within the chest drainage unit in order to restore normal operational negative pressure conditions. In addition, it has been observed that this adjustable check valve has proven to be difficult to manufacture.

There is found in U.S. Pat. No. 6,024,120 another negative pressure relief valve for relieving an excess negative pressure condition, that is configured so as to function either automatically or manually. In this valve, a diaphragm is slidably moved along a length of a piston rod. One end of the piston rod is configured so as to have a plurality or more of leg like members with a void between each leg. Thus, when the diaphragm slides over the leg like members, the suction side of the valve is put into fluid communication with the atmospheric side of the valve such that air flows into the chest drainage unit.

In this valve a seal must be maintained between the diaphragm and the exterior surface of the piston rod when the diaphragm is stationary and as it moves along the length of the piston rod until the suction side of the valve is put into fluid communication with the atmospheric side of the valve. If the seal is not maintained, the relief valve will leak air into the collection chamber or collection section side of the chest drainage unit. It is possible that the medical personnel could initially misinterpret such an air leak as being representative of the presence of an air leak upstream of the chest drainage, for example in the interconnecting tubing or at the drainage site (i.e., patient). In order to establish such a seal, the diaphragm must exert a radial force urging the inner periphery of the diaphragm into sealing engagement with the exterior surface of the piston rod. Because this force necessarily retards the motion of the diaphragm, it impacts the set point of the relief valve.

It thus would be desirable to provide a new automatic excess or high negative pressure relief valve that would respond to the negative pressure differentials typically seen in chest drainage units as well as chest drainage units and methods related thereto. It would be particularly desirable to provide such a pressure relief valve and related method that would more consistently open and close at the desired negative pressure conditions in comparison to prior art pressure relief valves/devices. It also would be desirable to provide such a pressure relief valve that is easily adjusted to any one of a number of negative pressure set points or within a range of negative pressures as compared to prior art pressure relief valves/devices. Such pressure relief valves preferably would be simple in construction, and less costly than prior art valves and such methods would not require highly skilled users to utilize the valves/device.

SUMMARY OF THE INVENTION

The present invention features an automatic high or excess negative pressure relief valve and methods related thereto. Such an automatic high or excess negative pressure relief valve when used in a chest drainage unit provides a mechanism to relieve excessively high negative pressure levels in that portion of the chest drainage unit in which liquid effluent from the patient is being collected, hereinafter generally referred to as the collection chamber. Also featured is such a high or excess negative pressure relief valve used in combination with any of a number of chest drainage units known to those skilled in the art, more particularly, chest drainage units characterized as having either wet or dry suction control and/or a wet or dry patient seal.

In its broadest aspects, such an automatic high or excess negative pressure relief valve includes a biasing mechanism that acts on a moveable member such that when the negative pressure level within a chamber, in which a portion of the relief valve is in fluid communication with, is less than a predetermined negative pressure value (i.e., less negative pressure condition) the moveable member is moved into sealing engagement with a sealing surface. When the negative pressure levels within this chamber are at or above the predetermined value (i.e., a larger or more negative pressure condition), the restoring force of the biasing mechanism is overcome and the moveable member moves away from the sealing surface, whereby air or other gaseous material is admitted into the chamber via the an automatic high or excess negative pressure relief valve.

In a more particular embodiment, the biasing mechanism is a spring member that acts on the moveable member, which spring member is configured and arranged so as to develop a force on the moveable member so as to have the above-described effect. It should be recognize that the biasing mechanism can be any of a number of mechanisms known to those skilled in the art that produces the above described biasing effect on the moveable member, including those that can be adapted for use in the present invention. As illustrative embodiments, such other biasing mechanisms include, but are not limited to a wave washer, diaphragm, leaf spring, hydraulic member, or pneumatic piston.

In another embodiment, the automatic high or excess negative pressure relief valve includes at least one first port in fluid communication with a gas source such as atmosphere and at least one second port in fluid communication with the chamber. In addition, the moveable member and the sealing surface are arranged so as to be disposed between the first port and the second port and so that when the moveable member is moved away from the sealing surface, the first and second ports are in fluid communication with each other, whereby gas from the gas source flows into the chamber.

According to one aspect of the present invention, the automatic high negative pressure relief valve includes a housing, a biasing mechanism, a sealing member moveable disposed within the housing, a flexible member and a seating surface. The flexible member is configured and arranged so as to extend between an interior of the housing and the sealing member so as to form a first and a second chamber within the housing, where the first chamber is fluidly coupled to a gas source and the second chamber is fluidly coupled to an interior of a vessel such that a pressure level within the second chamber corresponds to a pressure level within the vessel interior.

The biasing mechanism is disposed and arranged within the housing so as to act on the sealing member such that when the pressure level within the second chamber is less than a predetermined value (i.e., a less negative pressure condition) the sealing member is moved into sealing engagement with the seating surface. When the pressure level within the second chamber is at or above the predetermined value (i.e., a higher or more negative pressure condition), the restoring force of the biasing mechanism is overcome and the sealing member moves away from the seating surface, whereby gaseous material is admitted into the interior of the vessel via the an automatic high or excess negative pressure relief valve.

In a particular embodiment, the biasing mechanism comprises a spring, more specifically a spring under compression. The spring is configured and arranged so as to generate a force sufficient in magnitude to put the sealing member in sealing engagement with the seating surface when a differential pressure between the first and second chambers is less than a predetermined differential pressure value. The spring also is configured and arranged so the force that can be generated by the spring will allow the sealing member to move away from or be spaced from the seating surface when a differential pressure between the first and second chambers is at or above the predetermined differential pressure value. Stated another way, the spring force is established such that the sealing member is not prevented from moving away from or being spaced from the seating surface when a differential pressure between the first and second chambers is at or above the predetermined differential pressure value. As indicated hereinabove, the biasing mechanism is not limited to this particular embodiment as other biasing mechanism known to those skilled in the art are contemplated for use with the present invention.

The flexible member is configured (e.g., made of a material) so it essentially does not impose a force on the sealing member as the sealing member moves responsive to the biasing mechanism and differential pressure conditions. In particular embodiments, the flexible member is configured so it essentially does not impose a changing force on the sealing member as the sealing member moves responsive to the biasing mechanism and differential pressure or so that motion of the sealing member responsive to the biasing mechanism and differential pressures is essentially frictionless. More particularly, the flexible member is configured so it does not have, in effect, a spring rate that opposes motion of the sealing member responsive to the biasing mechanism and differential pressures. In this way, the spring force essentially establishes the opening and closing points of the automatic high negative pressure relief valve of the present invention. In an exemplary embodiment, the flexible member is a thin soft elastomer material.

In a further embodiment, the automatic high negative pressure relief valve includes a seating surface member that is configured and arranged to provide the seating surface for a portion of the sealing member, more particularly to provide a seating surface that sealingly engages a portion of a surface of the sealing member. In a particular embodiment, the seating surface member is configured and arranged to establish a seal between the seating surface member and the sealing member while minimizing the contact surface area therebetween. In a more particular embodiment, the seating surface member is conical in shape. More specifically, the conical seating surface member is configured and arranged so a portion of the exterior surface of the conical seating surface member sealingly engages the portion of the surface of the sealing member.

In more particular embodiments, the sealing member is configured so as to include a through aperture in the portion of the surface of the sealing member. In this embodiment, the exterior surface of the conical seating surface member sealingly engages interior portions of the through aperture. In a more specific embodiment, the exterior surfaces of the conical seating surface member are in edge or line contact with an interior edge of the through aperture.

In even a more particular embodiment, the sealing member is configured and arranged so as to include an extension member that extends outwardly from the surface of the sealing member. The extension member includes the through aperture, interior portions of which sealingly engage the exterior surface of the conical seating surface member. In an exemplary embodiment, the extension member is a tubular member. In a more specific embodiment, the exterior surfaces of the conical seating surface member are in edge or line contact with an interior edge of the through aperture of the extension member.

In an exemplary embodiment, the housing includes a cover member and a base. The cover member includes at least one, more particularly a plurality, more specifically a multiplicity of through apertures therein, the cover through apertures providing a fluid flowpath between the vessel interior and the second compartment. The base is configured and arranged so as to include at least one, more particularly a plurality, more specifically a multiplicity of through apertures or channels therein, where the through apertures or channels provide a fluid flowpath between the gas source and the first compartment. In a more particular embodiment, the base is configured and arranged so as to include the above-described seating surface member. In a more specific embodiment, the one or more apertures are arranged so as to be about and proximal the conically shaped seating surface member.

According to a second aspect of the present invention, the automatic high negative pressure relief valve includes a housing, a biasing mechanism, and a sealing member moveable disposed within a chamber in the housing. The housing is configured and arranged so that a surface of the chamber comprises a seating surface, a first through aperture is provided in the seating surface which aperture is in fluid communication with a gas source, such as atmosphere, and at least one, more particularly a plurality of second through apertures one end of each being fluidly coupled to the housing chamber and another ends of each being fluidly coupled to the interior of a vessel.

The biasing mechanism is disposed and arranged within the housing chamber so as to act on the sealing member such that when the pressure level within the one or more second through apertures is less than a predetermined value (i.e., a less negative pressure condition) the sealing member is moved into sealing engagement with the seating surface. When the pressure levels within the one or more second through apertures are at or above the predetermined value (i.e., a higher or more negative pressure condition), the restoring force of the biasing mechanism is overcome and the sealing member moves away from or is spaced from the seating surface, whereby gaseous material is admitted into the interior of the vessel via the an automatic high or excess negative pressure relief valve.

In a particular embodiment, the biasing mechanism comprises a spring, more specifically a spring under compression. The spring is configured and arranged so as to generate a force sufficient in magnitude to put the sealing member in sealing engagement with the seating surface when a differential pressure between the chamber and the first through aperture is less than a predetermined differential pressure value. The spring also is configured and arranged so the force that can be generated will allow the sealing member to move away from or be spaced from the seating surface when a differential pressure between the chamber and the first through aperture is at or above the predetermined differential pressure value. Stated another way, the spring force is such that it will not prevent the sealing member from moving away from the seating surface when a differential pressure between the chamber and the first through aperture is at or above the predetermined differential pressure value. In an exemplary embodiment, the sealing member includes an aperture in which is received the spring or biasing mechanism.

According to a third aspect of the present invention, an automatic high-negative pressure relief valve, including those described hereinabove, is configured and arranged so as to include a mechanism for selectively adjusting the biasing mechanism so as to selectively adjust the force being applied to or acting on the sealing member by the biasing mechanism. In this way, one can in adjust the set point of the relief valve (i.e., when the valve will open). In the case where the biasing mechanism comprises a spring, the adjusting mechanism selectively compresses and decompresses the spring, thereby adjusting the spring force being applied to sealing member.

In an illustrative embodiment, the adjusting mechanism is threadably disposed within a threaded aperture in the housing such that rotation of the adjusting mechanism in one of a counter-clockwise or clockwise direction causes the biasing mechanism to be adjusted so as to increase or decrease the force being applied to the sealing member. In an illustrative exemplary embodiment, the adjusting mechanism is a threaded member, one end of which is configured and arranged so as to engage an end of the spring comprising the biasing mechanism such that the spring is selectively compressed or de-compressed responsive to the direction of rotation and the amount of rotation of the threaded member. In further specific embodiments, the adjusting mechanism and the housing cooperate so that the adjusting mechanism is sealing disposed within the housing.

According to fourth aspect of the present invention, an automatic high-negative pressure relief valve, including those described hereinabove is configured and arranged so as to include a filtering mechanism being configured and arranged to filter incoming gas (e.g., air) from the gas source (e.g., atmosphere) prior to it flowing into the interior of the vessel such as the collection chamber of a chest drainage unit. In an exemplary embodiment, the filtering mechanism comprises any of a number of filtering mediums known to those skilled in the art by which the gas from the gas source is filtered to a desired state/condition before being passed to the vessel interior.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 1:
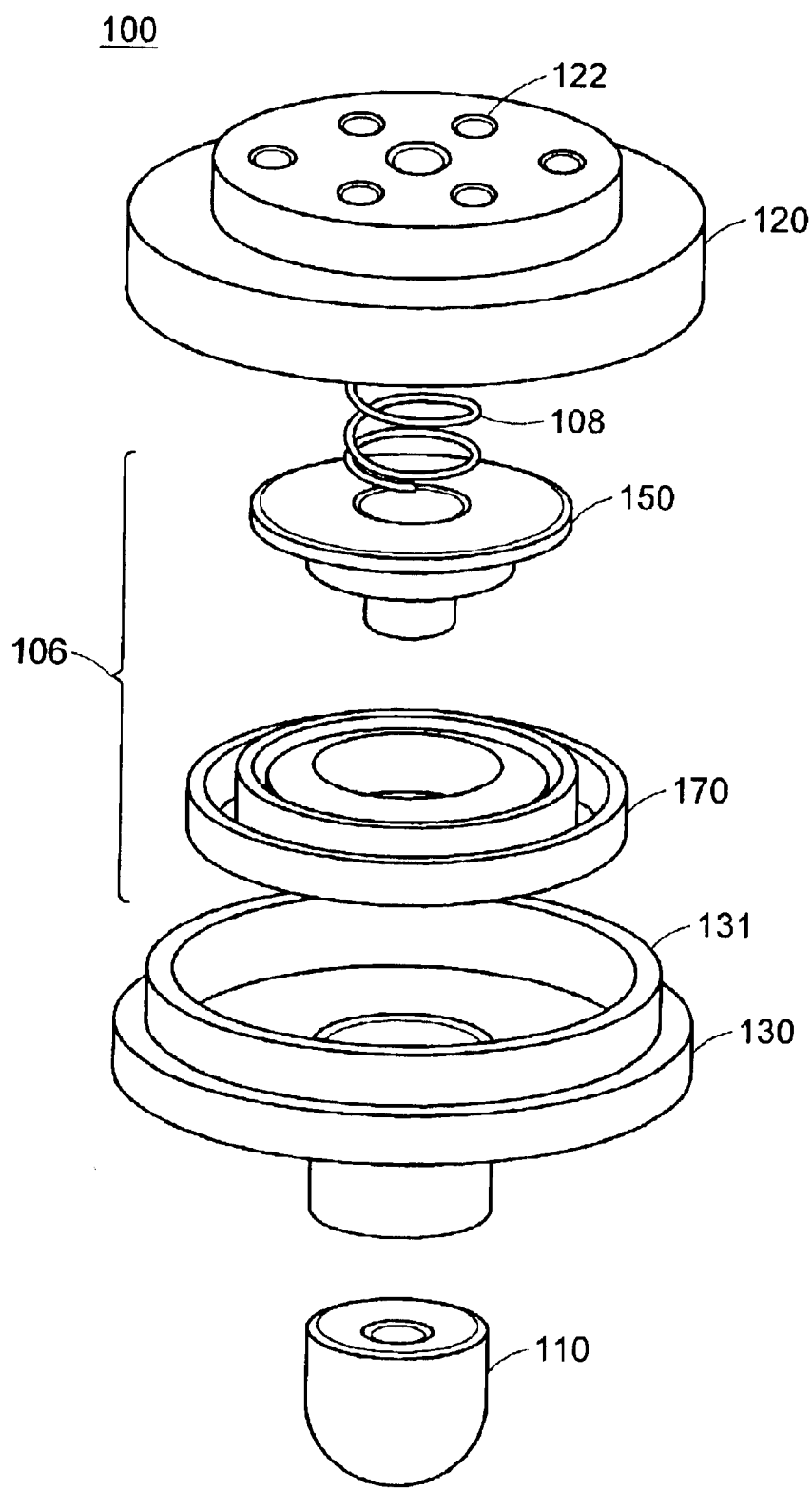
FIG. 1 is an exploded view of an automatic high-negative pressure relief valve according to one aspect of the present invention.

Referring now to the various figures of the drawing wherein like reference characters refer to like parts, there is shown in FIGS. 1–4 various views of an automatic high-negative pressure relief valve 100 according to one aspect of the present invention. The components making up such an automatic high-negative pressure relief valve 100 cooperate such that the valve includes a housing 102 having an interior compartment 104, and a sealing subassembly 106, where the sealing subassembly 106 as described hereinafter, is moveably disposed within the housing interior compartment 104. Also the housing 102 and the sealing subassembly 106 cooperate so as to sub-divide the interior compartment 104 into two sub-compartments, a first sub-compartment 105a and a second sub-compartment 105b. The automatic high-negative pressure relief valve 100 also includes a mechanism for biasing the seal assembly 106 into sealing engagement with the housing 102. In a further embodiment, the automatic high-negative pressure relief valve 100 further includes a filter element 110 as hereinafter described.

In the illustrated embodiment, the mechanism for biasing comprises a spring 108, such as coil spring. It should be recognize that the biasing mechanism can be any of a number of mechanisms known to those skilled in the art that produces the herein described biasing effect on the sealing subassembly 106, including those that can be adapted for use in the present invention. As illustrative embodiments, such other biasing mechanisms include, but are not limited to a wave washer, diaphragm, leaf spring, hydraulic member, or pneumatic piston.

The housing 102 includes a top cap 120 and a bottom cap 130 that are joined together using any of a number of techniques known to those skilled in the art so as to form the housing and the interior compartment 104 thereof. The top and bottom caps 120, 130 each include a mating connection 121, 131 that are configured and arranged using any of a number of techniques known to those skilled in the art for mating the top and bottom caps together. In the illustrated embodiment, the top cap mating connection 121 comprise an annular aperture and the bottom cap mating connection 131 comprises a circular wall member that extends upwardly so as to be received within the annular aperture. Such mating connections 121, 131 alone (e.g., using a press or interference fit) or in combination with other techniques such as the use of adhesives or welding (e.g., ultrasonic, thermal) to form a mechanical connection therebetween so as to form the housing 102.

The top cap 120 is configured so as to include one or more, more particularly a plurality of through apertures 122. The top cap through apertures 122 are not particularly limited to a given number or size, however, the number and size of the top cap through apertures is generally set or established so as to provide a predetermined and desired flow area.

Figure 8A:
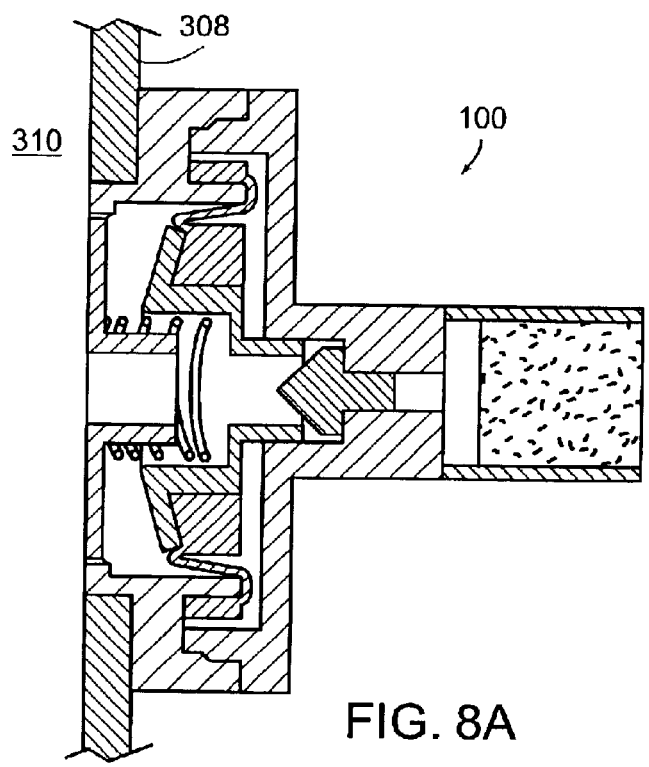
FIGS. 8A,B are cross-sectional side views through a portion of an illustrative chest drainage unit illustrating installations of an automatic high-pressure negative relief valve according to the present invention.
Figure 8B:
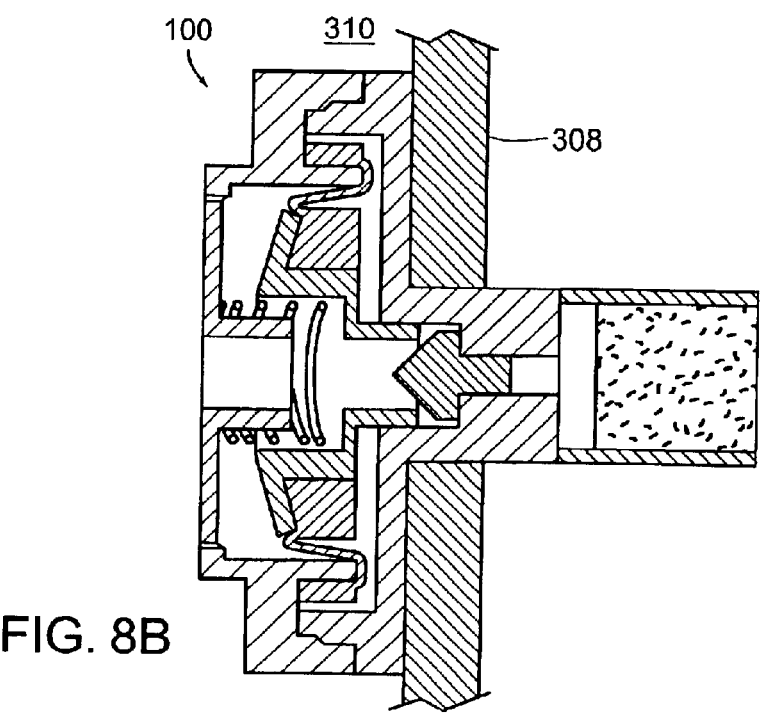
Figure 9:
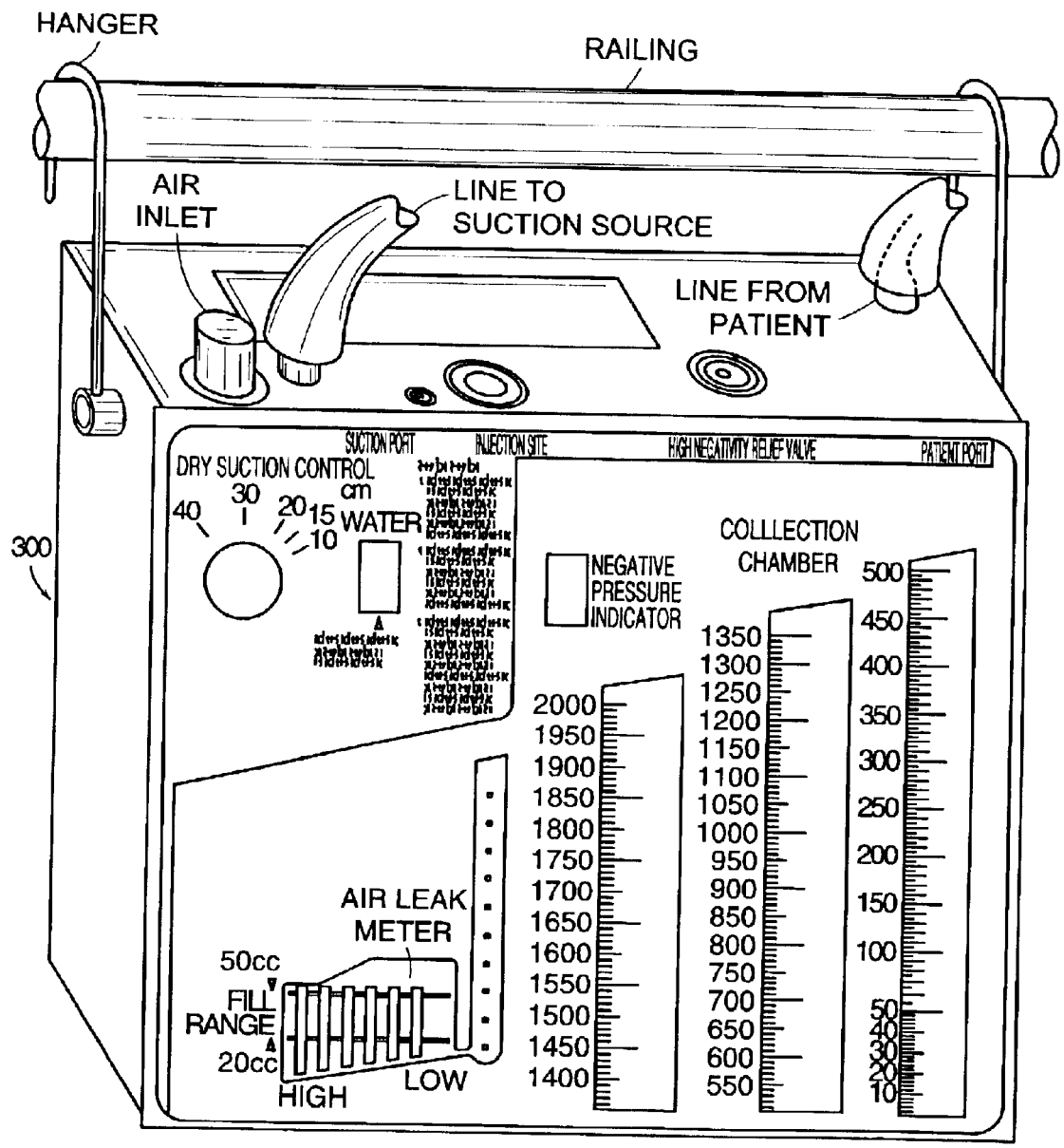
FIG. 9 is an axonometric schematic view of an exemplary chest drainage unit according to the present invention.
Figure 10:
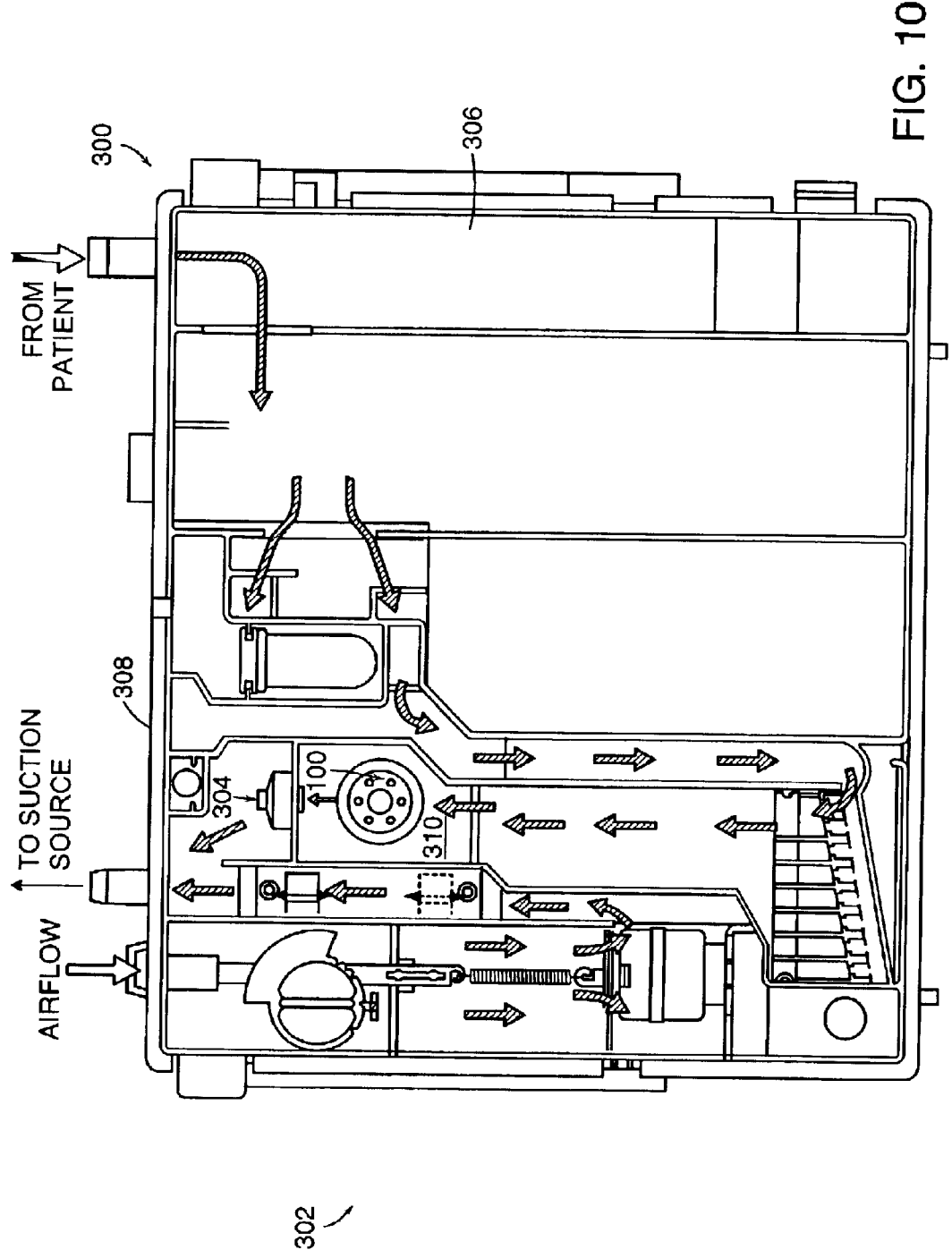
FIG. 10 is a cross-sectional front view of the chest drainage unit of FIG. 9 showing an automatic high-negative pressure relief valve according to the present invention with the front panel removed for clarity.

Each of the top cap through apertures 122 are located in the top cap 120 so each are in fluid communication with the first sub-compartment 105a and with the interior of the vessel having protection from high-negative pressure conditions. In a particular application, the top cap through apertures 122 are in fluid communication with the volume/interior 310 (FIGS. 8A,B & 10) of the housing 308 comprising the chest drainage unit 300 (FIGS. 9–10). In this way, the pressure being developed in the first sub-compartment 105a of the automatic high-negative pressure relief valve 100 follows the pressure conditions within the interior volume of a vessel having protection from high-negative pressure conditions. More particularly, the pressure being developed in the first sub-compartment 105a of the automatic high-negative pressure relief valve 100 follows the pressure conditions within the chest drainage unit 300, more specifically the pressure conditions that exist within the collection chamber 306 thereof.

The top cap 120 also includes a post member 126 that extends from the top cap into the first sub-compartment 105a. The post member 126 is configured and sized so the spring 108 is mounted about the post member and so as to limit lateral deflection and movement of the spring 108 when it is being compressed. Although the illustrated embodiment depicts the post member 126 as a hollow tubular member, the post member shall not be so particularly limited as the post member can be a hollow or solid and can be of any geometric shape appropriate for the intended use. For example, the post member 126 can have a polygonal cross-section (e.g., octagon). It should be recognized that the support mechanism for the biasing mechanism is not limited to a post type of member but also includes any of a number of support mechanisms/techniques that are appropriate for the particular form of the biasing mechanism.

Figure 2:
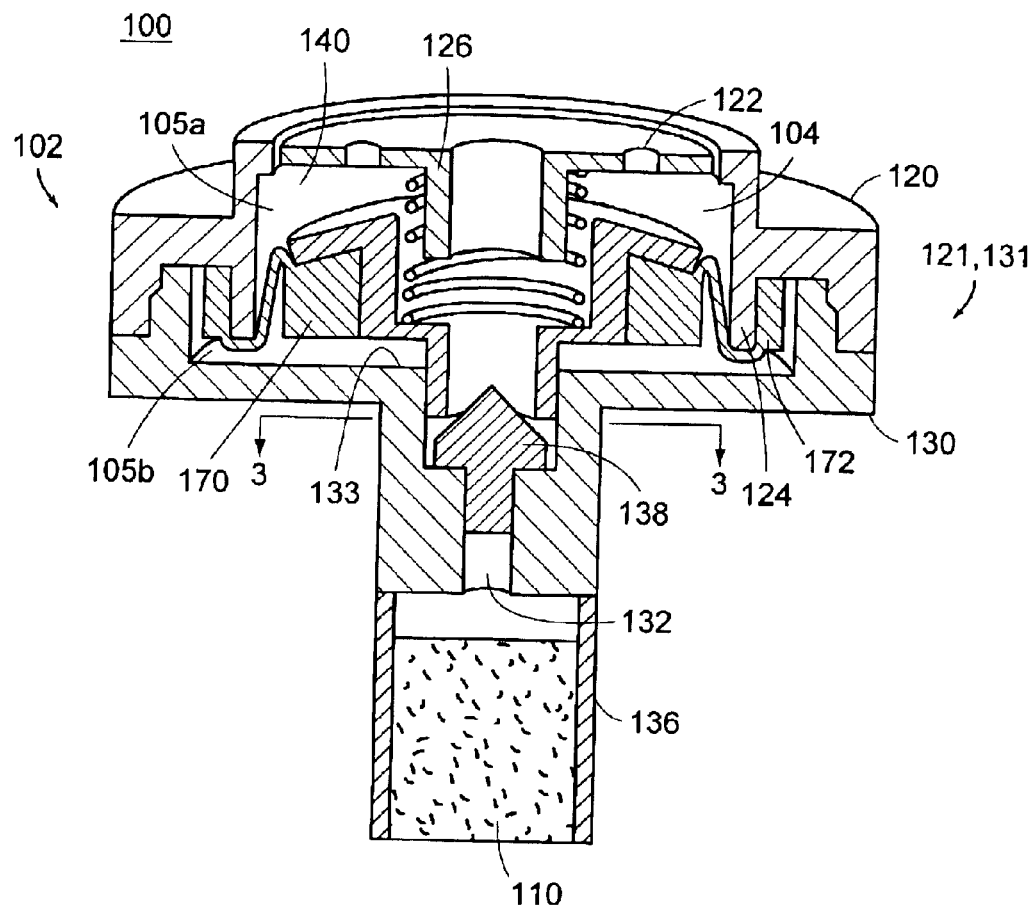
FIG. 2 is a cross-sectional side view of the automatic high-pressure negative relief valve of FIG. 1.
Figure 3:
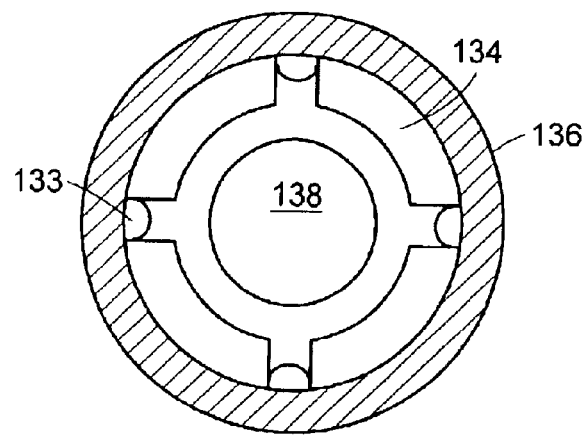
FIG. 3 is a cross-sectional view of the atmospheric inlet end of the automatic high-pressure negative relief valve taken along line 3—3 of FIG. 2.
Figure 4A:
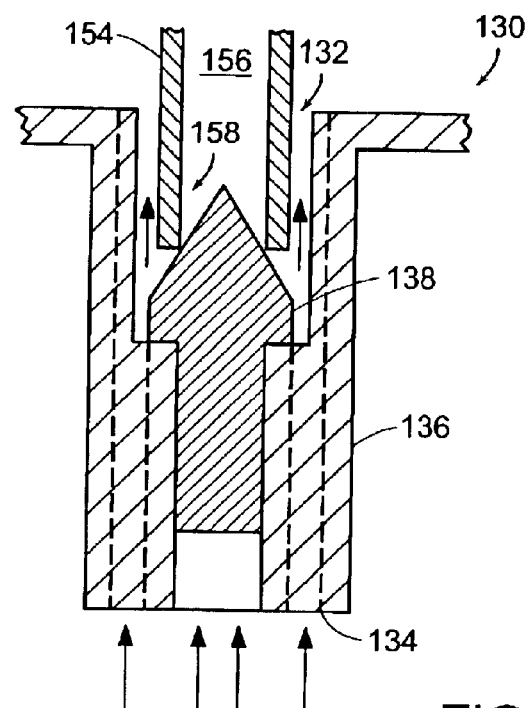
FIGS. 4A,B are cross-sectional side views of the atmospheric inlet end of the automatic high-pressure negative relief valve of FIG. 1, when the valve is in a closed state (4A) and an open state (4B)

Correspondingly, and as more clearly seen in FIGS. 2–3 and 4A, B, a portion of the bottom cap 130 includes a through aperture 132 that is made up of a plurality of flow passages 134. The bottom cap 130 also is configured and arranged so that one end of this through aperture 132 is in fluid communication with the second sub-compartment 105b and so that the other end thereof is in fluid communication with the gas or fluid source, such as atmosphere. In more specific embodiments, the one end of the through aperture is in fluid communication with the gas or fluid source via the filter element 110 (see FIG. 2). In this way, the pressure being developed in the second sub-compartment 105b of the automatic high-negative pressure relief valve 100 corresponds to the pressure conditions of the gas or fluid source. In the case of a chest drainage unit, this would correspond to atmospheric pressure conditions. In the illustrated embodiment, the bottom cap 130 includes a tubular projection 136 that extends outwardly from the main portion of the bottom cap, which tubular member essentially includes the through aperture 132 as well as the plurality of flow passages 134.

The bottom cap 130 also includes a valve seat seal member 138 that is disposed within the bottom cap through aperture 132, more particularly in a portion of the through aperture including the plurality of flow passages 134. In the illustrated embodiment, the valve seat seal member 138 is spaced and supported from interior surfaces of the through aperture 132 by a plurality of radially extending ribs 133 or support members so as to form the plurality of flow passages 134. In a more specific embodiment, the support substructure for the valve seat seal number 138 includes the plurality of ribs 133 and a platform member secured thereto, where the valve seat seal member is secured to the platform. The plurality of flow passages 134 also are formed so that they extend along the length of the through aperture 132 as shown in FIGS. 4A,B or so the flow passages 134' extend part way in the tubular projection 136' along the length of the through aperture as shown in FIGS. 4C,D.

The valve seat seal member 138 is configured and arranged so as to cooperate with a portion of the sealing subassembly 106 to form a fluid or pressure boundary between the first and second sub-compartments 105a,b when the valve is in the closed position as is shown more clearly in FIGS. 4A,C. In more particular embodiments, the valve seat seal member 138 is made from a material, such as a soft elastomeric material or any of a number of other materials known to those skilled in the art having a shore durometer from about 20 to 50, more particularly a shore durometer of about 30 to 40, to further facilitate the formation of the fluid/pressure boundary with the sealing subassembly 106. In a more specific embodiment, the valve seat seal member 138 further includes a coating, such as silicone fluid, to lubricate the valve seat and also to further facilitate the formation of a fluid/pressure boundary with the sealing subassembly 106. In an illustrative exemplary embodiment, the valve seat seal member 138 is conically shaped so the valve seat seal member is essentially in line or edge sealing contact with said portion of the sealing sub-assembly 106 to form the fluid/pressure boundary. The formation of the fluid/pressure boundary also is described further below.

As is illustrated in FIGS. 2 and 4A–D and described further below, a portion of the sealing subassembly 106 is slidably received in the upper portion of the bottom cap through aperture 132. In this way, the pressure within the second sub-compartment 105b generally corresponds to the pressure of the gas/fluid source or atmosphere, when the automatic high-negative pressure relief valve is in the closed position (see FIGS. 4A,C).

Figure 5:
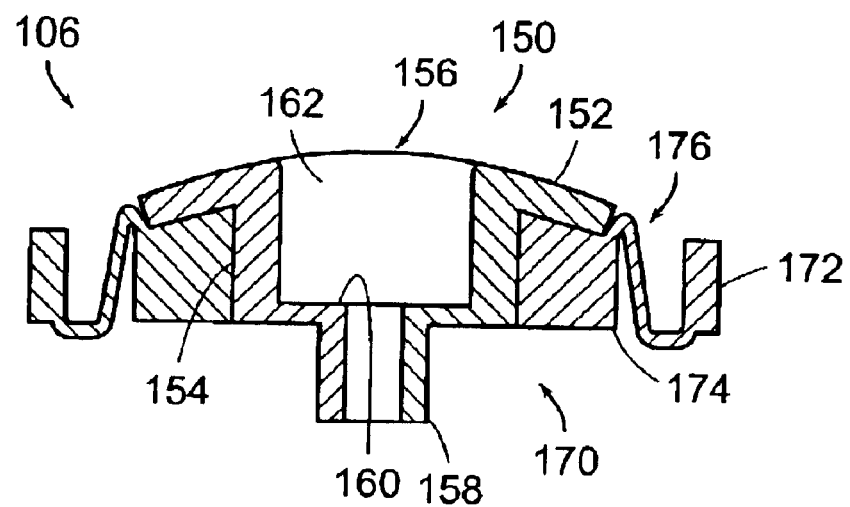
FIG. 5 is a cross-sectional view of the sealing subassembly.

Now referring also to FIG. 5, the sealing subassembly 106 includes a floating seal member 150 and a rolling seal member 170 that are mechanically secured to each other as hereinafter described so that the sealing subassembly moves as a unitary structure when the differential pressure developed across the sealing subassembly is in excess of a predetermined value. The floating seal member 150 includes a flange 152 and a fluid passage member 154, where the fluid passage member extends outwardly from a bottom surface of the flange. In a more particular embodiment, the fluid passage member 154 is located so a long axis thereof extends outwardly from the approximate center point of the flange 152.

The flange 152 extends outwardly from the fluid passage member 154 so as to provide a surface that mechanically engages an opposing surface of the rolling seal member 170 as hereinafter described. In a particularly illustrative embodiment, the flange 152 is dish shaped, however, this shall not be construed as being a limitation as the flange can have a number of geometric shapes (e.g., a flat circular member) otherwise consistent with the functions described herein for the automatic high-pressure relief valve 100 of the present invention.

The flange 152 and the fluid passage member 154 also are configured and arranged so as to provide a through aperture 156 that extends from a top surface of the flange to a seating end 158 of the fluid passage member. In a particular embodiment, the through aperture 156 is essentially parallel to a long axis of the fluid passage member 154. The through aperture 156 is sized so at least a desired fluid or gas flow is attained so the negative pressure condition within a collection chamber 306 of a chest drainage 300 (FIGS. 9–10) is returned to desired operational conditions within a specified and desired period of time.

In the illustrated embodiment (e.g., see FIG. 5) the through aperture 156 is configured with an internal step 160 that defines an upper portion 162 for the through aperture. As shown in FIG. 2, the spring 108 is received in the through aperture upper portion 162 and one end of the spring rests upon or is supported by the internal step 160. As such, the through aperture portion 162 is generally sized to receive the spring 108 therein and so the spring does not generally deflect or move laterally as the spring is compressed. In addition, the internal step 160 is sized to support the one end of the spring 108 when the spring is disposed in the through aperture upper portion 162 and so the one end of the spring is in mechanical engagement with the sealing subassembly 106 as shown in FIG. 2. Such mechanical engagement is one part of the mechanism by which the sealing subassembly 106 is put into sealing engagement with the housing 102, more particularly the valve seat seal member 138.

In addition, the top cap 120 is configured so a long axis of the top cap post member 126 is generally aligned with the long axis of the through aperture 156. This provides a mechanism by which the spring 108 or other biasing mechanism is generally aligned so that the force generated by the differential pressure developed across the sealing subassembly 106 also should act along a long axis of the spring. In this way, the force being generated by the differential pressure should generally cause the spring to compress or relax.

When the top and bottom caps 120, 130 are secured together to form the housing 102, the spring 108 is compressed between the top and bottom caps a predetermined amount. The amount of compression and other characteristics of the spring 108 establish a preset differential pressure set point(s) for opening and closing the relief valve 100. As herein described, when the differential pressure is below the set point the spring force keeps the automatic high-negative pressure relief valve 100 in a closed condition and when the differential pressure exceeds the set point (i.e., the pressure with the chest drainage unit becomes more negative), the relief valve opens causing the spring 108 to be compressed further. As the pressure within the chest drainage unit 300 (FIGS. 9–10) is reduced to normal operating conditions, the spring 108 relaxes and returns the relief valve 100 to the closed position. In some chest drainage units with a dry suction control regulation device that is designed to maintain suction pressures at negative pressures up to and including −40 cm of water, the set point for the automatic negative pressure relief valve is typically set at a negative pressure of about −50 cm of water.

It should be recognized that the present invention is not limited to the use of a stepped through aperture as the mechanism for mechanically engaging the sealing subassembly 106 and the spring 108. It is within the scope of the present invention for the flange 152 and/or the fluid passage member 154 to be configured using any of a number of techniques known to those skilled in the art by which the spring 108 or other biasing mechanism can be mechanically engaged with the sealing subassembly 106. For example, the flange 152 and the fluid passage member 154 can be configured with an annular aperture spaced from and about the through aperture 156 and the spring 108 is disposed in the annular aperture.

The rolling seal member 170 includes a distal end portion 172, a skirt portion 174 and a flexible portion 176 that interconnects the end portion and the skirt portion. The rolling seal member skirt portion 174 is configured so as to be generally complementary of the shape of a portion of the outer surface of the fluid passage member 154 and the flange 152. Additionally, the inner diameter or cross-section of the rolling seal member skirt portion 174 is generally established so the skirt portion remains in mechanical and sealing engagement with the outer surface of the fluid passage member 154 during normal motion of the sealing subassembly 106, as hereinafter described, responsive to changes in differential pressure developed across the sealing subassembly. In a more specific example, a press fit is established between this portion of the outer surface of the fluid passage member 154 and the skirt portion 174. It also is within the scope of the present invention for the skirt portion 174 to be mechanically secured to the outer surface of the fluid passage member 154 using any of a number of techniques known to those skilled in the art such as securing by means of adhesives, vibration welding or welding using ultrasonic or thermal energy.

The rolling seal member distal end portion 172 is configured and arranged so as to be generally complementary of the shape of an annular wall member 124 of the top cap 120. Additionally, the rolling seal member distal end portion 172 is generally configured and arranged so the distal end portion remains in mechanical and sealing engagement with the annular surfaces of the top cap wall member 124 during normal motion of the sealing subassembly 106 as hereinafter described responsive to changes in differential pressure developed across the sealing subassembly. More particularly, the distal end portion 172 is configured and arranged so as to mechanically and elastically secure the distal end portion to the top cap wall member 124. It also is within the scope of the present invention for the distal end portion 172 to be mechanically secured to the distal end portion of the top cap wall member 124 using any of a number of techniques known to those skilled in the art such as securing by adhesives or welding (e.g., vibration, ultrasonic and thermal).

Preferably, the rolling seal member distal end portion 172 also is configured so that the distal end portion in combination with the flexible portion 176 allows the sealing subassembly 106 to move freely with respect to the top and bottom caps 120, 130 and the housing 102 and without imposing a force that acts on the moving sealing subassembly.

The rolling seal member 170 by means of its mechanical and sealing engagement with the floating seal member 150 and its mechanical and sealing engagement with the top cap wall member 124, subdivides the housing interior compartment 104 so as to define the first sub-compartment 105a and the second sub-compartment 105b.

When the automatic high-negative pressure relief valve 100 is in the closed position, as illustrated in FIG. 4A, the fluid passage member seating end 158 is put into sealing engagement with the seating surface of the seating seal member 138. This generally corresponds to the case where the suction pressure applied within the chest drainage unit collection chamber 306 is at or below (i.e., less negative) the predetermined suction pressure, the suction pressure generally corresponding to the set point of the automatic high-negative pressure relief valve 100.

In a more particular embodiment, the seating seal member 138 and the fluid passage seating end 158 are configured and arranged so as to minimize the contact area comprising the fluid/pressure boundary formed when the fluid passage member seating end is put into sealing engagement with the seating surface of the seating seal member. In a more specific embodiment, the seating seal member 138 is conical and interior surfaces of the fluid passage member seating end 158 are put into sealing engagement with the seating surface of the seating seal member, in particular the interior surfaces are in line or edge contact with the seating surface of the seating seal member 138.

Figure 4B:
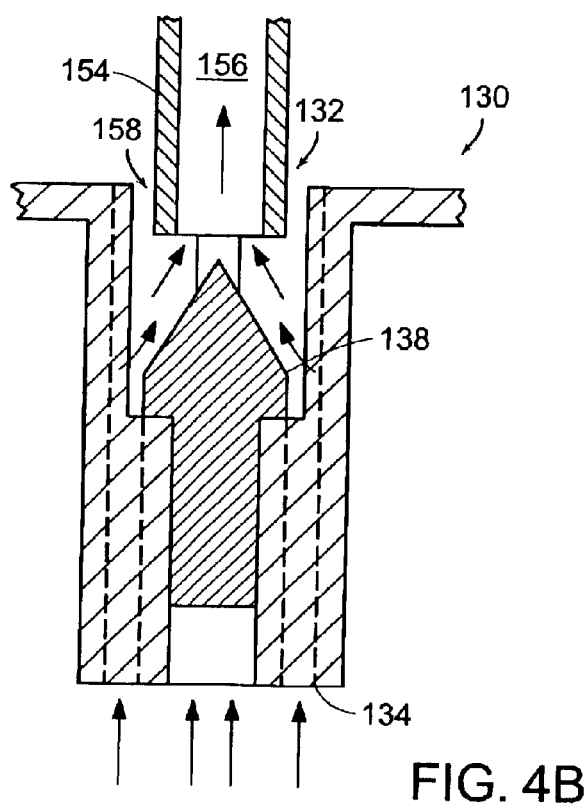
FIGS. 4C,D are cross-sectional side views of an alternative atmospheric inlet end, when the valve is in a closed state (4C) and an open state (4D)
Figure 4C:
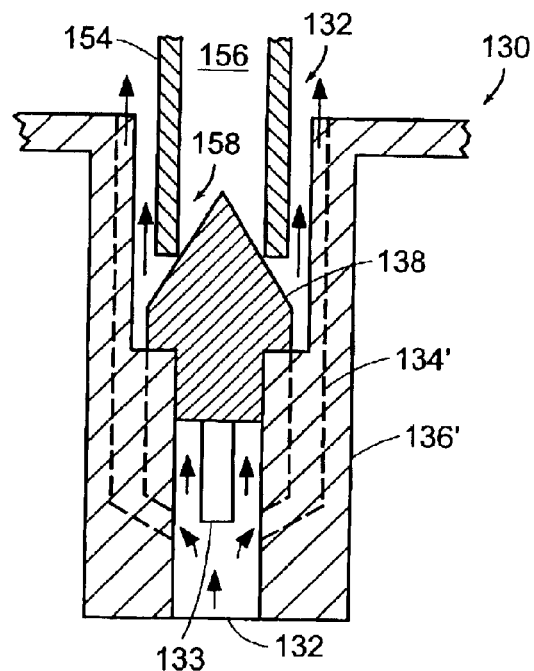
Figure 4D:
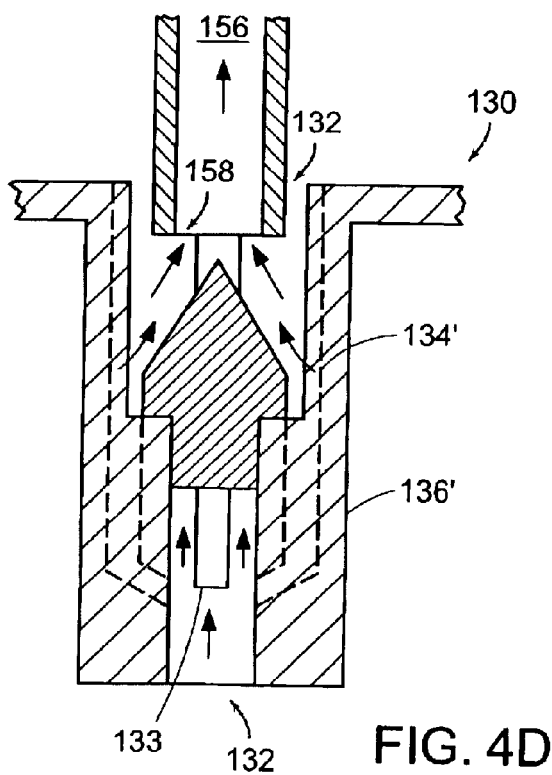

Conversely, when the automatic high-negative pressure relief valve 100 is put in the open position, as illustrated in FIG. 4B, the seating end 158 of the fluid passage member 154 moves away from or is spaced from the seating surface of the seating seal member 138. This generally corresponds to the case where the suction pressure being imposed is greater than the predetermined suction pressure (i.e., pressure is more negative). Concurrently, the rolling seal member flexible portion 176 automatically reconfigures itself (e.g., rolls) responsive to this motion of the sealing subassembly 106 so as to maintain the pressure boundary between the first and second sub-compartments 105a,b.

The flexible portion 176 rolls or reconfigures itself without imposing a force or drag on the motion of the sealing subassembly 106 while maintaining the integrity of the pressure boundary described above. More particularly, the flexible portion 176 rolls or re-configures itself essentially without imposing a changing force, that is without imposing a force that would change as a function of the position and/or direction of motion of the sealing subassembly 106 as it moves with respect to the seating seal member 138. In other words, the flexible portion 176 allows the sealing subassembly to move with respect to the seating seal member 138 without frictional losses or without imposing a spring rate. In this way, the motion of the sealing subassembly 106 is not dampened by the flexible member 176.

When the automatic high-negative pressure relief valve 100 is put into the open position the first sub-compartment 105a is no longer isolated from the second sub-compartment 105b as the through aperture 156 is fluidly coupled to the bottom cap through aperture 132. Thus, each of the top cap through apertures 122 also are fluidly coupled to the bottom cap through aperture 132 so that atmospheric air or gas from the gas source is admitted into the interior of the vessel having over pressure protection, such as the interior volume of a chest drainage unit so as to reduce the suction pressure or degree of vacuum being developed within the chest drainage device 300 and more specifically the collection chamber 306 thereof. As indicated above, the selectively pre-compressed coil spring 108 provides a mechanism by which a portion of the sealing subassembly 106 (i.e., the seating end 158) is placed into sealing engagement with the bottom cap seating seal member 138 or moved away therefrom when the actual suction pressure exceeds the selected or desired suction pressure.

Figure 6:
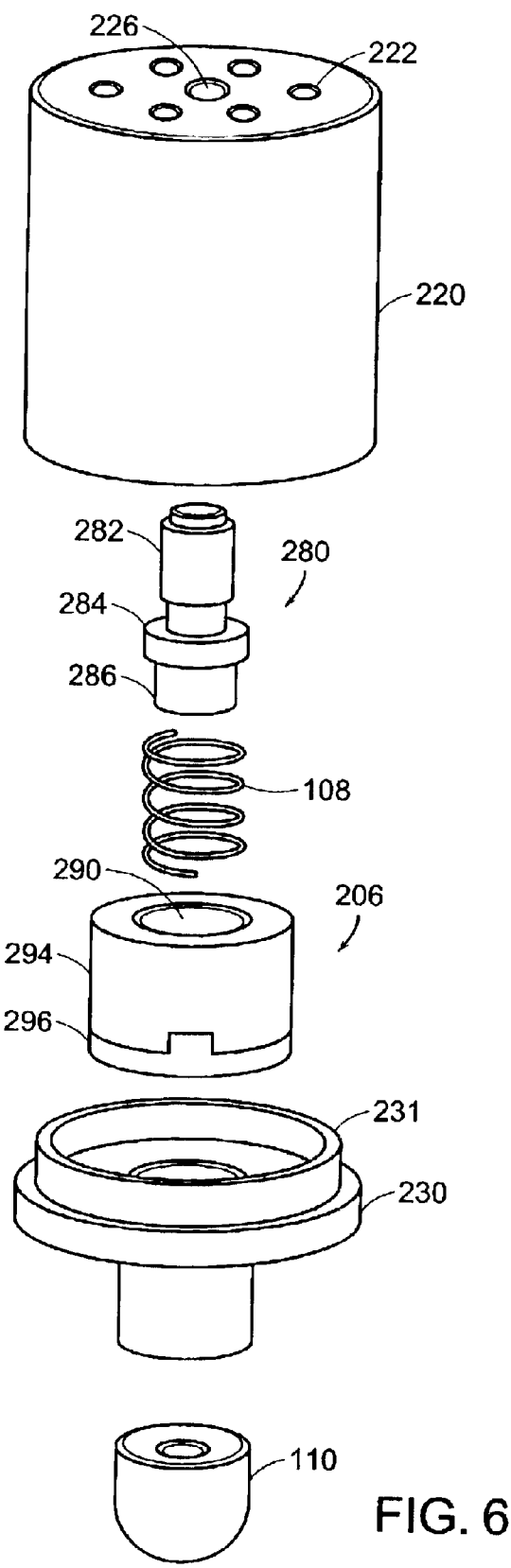
FIG. 6 is an exploded view of an automatic high negative pressure relief valve according to other aspects of the present invention.

Now referring to FIGS. 6–7 there is shown an automatic high-negative pressure relief valve 200 according to other aspects of the present invention. The components making up such an automatic high-negative pressure relief valve 200 cooperate so that the valve includes a housing 202 having an interior compartment 204 and a sealing subassembly 206, where the sealing subassembly 206, as described hereinafter, is moveably disposed within the housing interior compartment 204. The automatic high-negative pressure relief valve 200 also includes a mechanism for biasing the seal assembly 206 into sealing engagement with the housing 202. In the illustrated embodiment, the mechanism for biasing comprises a spring 108, such as coil spring and further includes an adjustment mechanism 280 to adjust the compression of the spring 108. In a further embodiment, the automatic high-negative pressure relief valve 200 further includes a filter element 110 as hereinafter described.

The housing 202 includes a top cap 220 and a bottom cap 230 that are joined together using any of a number of techniques known to those skilled in the art so as to form the housing and the interior compartment 204 thereof. The top and bottom caps 220, 230 each include a mating connection 221, 231 that are configured and arranged using any of a number of techniques known to those skilled in the art for mating the top and bottom caps together. In the illustrated embodiment, the top cap mating connection 221 comprise a recess formed in the interior surface of the top cap and the bottom cap mating connection 131 comprises a circular wall member that extends upwardly so as to be mate with the recess so that when joined a ship-lap type of joint is established. Such mating connections 221, 231 alone (e.g., using a press or interference fit) or in combination with other techniques such as the use of adhesives or welding (e.g., ultrasonic, thermal) to form a mechanical connection there between so as to form the housing 202. Alternatively, the top and bottom caps 220, 230 can be configured so as to include an annular ring and a circular wall as the mating connections as described hereinabove.

The top cap 220 is configured so as to include one or more, more particularly a plurality of through apertures 222. The top cap through apertures 222 are not particularly limited to a given number or size, however, the number and size of the top cap through apertures is generally set or established so as to provide a predetermined and desired flow area. Each of the top cap through apertures 222 are located in the top cap 220 so each are fluidly coupled to the interior compartment 204 and with the interior of the vessel having protection from high-negative pressure conditions. In a particular application, the top cap through apertures 222 are in fluid communication with the volume/interior 310 (FIGS. 8A,B) of the housing 308 comprising the chest drainage unit 300 (FIGS. 9–10). In this way, the pressure being developed in the housing interior compartment 204 of the automatic high-negative pressure relief valve 200 follows the pressure conditions within the interior volume of a vessel having protection from high-negative pressure conditions. More particularly, the pressure being developed in the housing interior compartment 204 of the automatic high-negative pressure relief valve 200 follows the pressure conditions within the chest drainage unit 300, more specifically the pressure conditions that exist within the collection chamber 306 thereof.

As also described below the top cap 220 further includes an adjustment aperture 226 in which is disposed the adjustment mechanism for the biasing device. It should be recognized, however, that the top cap 220 of the automatic high-negative pressure relief valve 200 also is configurable so the biasing mechanism (e.g., the spring 108) is not adjustable. Thus, in an alternative embodiment, the top cap 220 is configured with a post member such as that described above to which is mounted the spring 108 in the fashion described above. Reference shall be made to the foregoing discussion regarding FIGS. 1–4, regarding other biasing mechanisms contemplated for use with an automatic high-negative pressure relief valve according to the present invention.

The adjustment mechanism 280 includes an upper portion 282, an intermediate portion 284 and a lower portion 286. Correspondingly, the top cap adjustment aperture 226 is configured with an upper portion 227a, an intermediate portion 227b and a lower portion 227c.

The adjustment mechanism lower portion 286 is configured and sized so the spring 108 is mounted about the lower portion and so as to limit lateral deflection and movement of the spring 108 when it is being compressed. Although the illustrated embodiment depicts the lower portion 286 as a cylindrical member this is not particularly limiting, as the lower portion can be of any geometric shape appropriate for the intended use, for example, the lower portion 286 can have a polygonal cross-section (e.g., octagon). Correspondingly, the adjustment aperture lower portion 227c is configured and sized to receive the spring 108 and the adjustment mechanism therein. More particularly, the adjustment aperture lower portion 227c is sized to limit deflection or lateral movement of the spring 108 as it is compressed.

The adjustment mechanism intermediate portion 284 is generally configured and arranged to extend outwardly from the outer surface of the adjustment mechanism so as to form a lip (e.g., a radially extending lip) that lies within the confines of the adjustment aperture lower portion 227a. One end of the spring 108 mechanically engages the lip formed by the adjustment mechanism intermediate portion 284 so the spring can be compressed or relaxed by the rotational motion of the adjustment mechanism. Thus, the lip acts like a stop for the spring 108.

The adjustment mechanism intermediate portion 284 and the adjustment aperture intermediate portion 227b cooperate so as to limit travel of the adjustment mechanism 280 within the top cap adjustment aperture 226. In the illustrated embodiment, the adjustment aperture intermediate portion 227b is in the form of a sloping surface. Thus, as the adjustment mechanism 280 moves longitudinally outwardly, the adjustment mechanism intermediate portion 227b contacts the sloping surface retarding further longitudinal motion. It should be recognized that the foregoing is illustrative of one technique for retarding such longitudinal motion and thus is not particularly limiting as any of a number of techniques can be adapted for use with the present invention. For example, the top cap adjustment aperture 226 can be formed as a stepped aperture, where longitudinal motion is restrained when the adjustment mechanism intermediate portion 227b contacts the step.

In one embodiment, the adjustment mechanism upper portion 282 and the adjustment aperture upper portion 227a are configured and arranged so as to form a threaded connection, whereby the adjustment mechanism 280 can be rotated within the adjustment aperture 226 so as to cause the spring to be compressed or relaxed. This is particularly advantageous because it provides a mechanism by which a manufacturer can adjust the amount of compression of the spring 108 so the desired compressive force is achieved and thus compensate for any deviations occurring doing manufacturing or differences in material properties. Consequently, this capability to compensate for manufacturing tolerances, characteristics or properties of the spring 108 and other manufacturing deviations tends to increase manufacturing flexibility.

It should be recognized that any other mechanism known to those skilled in the art can be used to selectively adjust the biasing mechanism and thereby the set point of an automatic high-negative pressure relief valve according to the present invention. For example, and in an alternative embodiment, a sliding fit is formed between the top cap adjustment aperture 226 and the adjusting mechanism 280, more particularly between the adjustment aperture upper portion 227a and the adjustment mechanism upper portion 282. In this way, the manufacturer can move the adjusting mechanism 280 in and out within the top cap adjustment aperture 226 until the desired amount of compression force is achieved. Thereafter, the adjusting mechanism 280 is secured or fixed in place within the top cap adjustment aperture using any of a number of techniques known to those skilled in the art including adhesives or welding (e.g., ultrasonic, vibration, thermal). It also is within the scope of the present invention for one or both of the opposing sliding surfaces to include surface artifacts such as detents therein to further facilitate the adjusting and/or securing process.

The bottom cap 230 is configured and arranged so a surface thereof forming part of the housing interior compartment 204 comprises a seating seal surface 232 and to include a fluid passage member 234 including a through aperture 236. The bottom cap 230 also is configured and arranged so that one end of the through aperture 236 is formed in the seating seal surface 232 and so that the other end thereof is in fluid communication with the gas or fluid source, such as atmosphere, via the filter element 110 (see FIGS. 7A,B). In this way, the pressure within the bottom cap through aperture 236 corresponds to the pressure conditions of the gas or fluid source. In the case of a chest drainage unit 300, this would correspond to atmospheric pressure conditions.

Figure 7A:
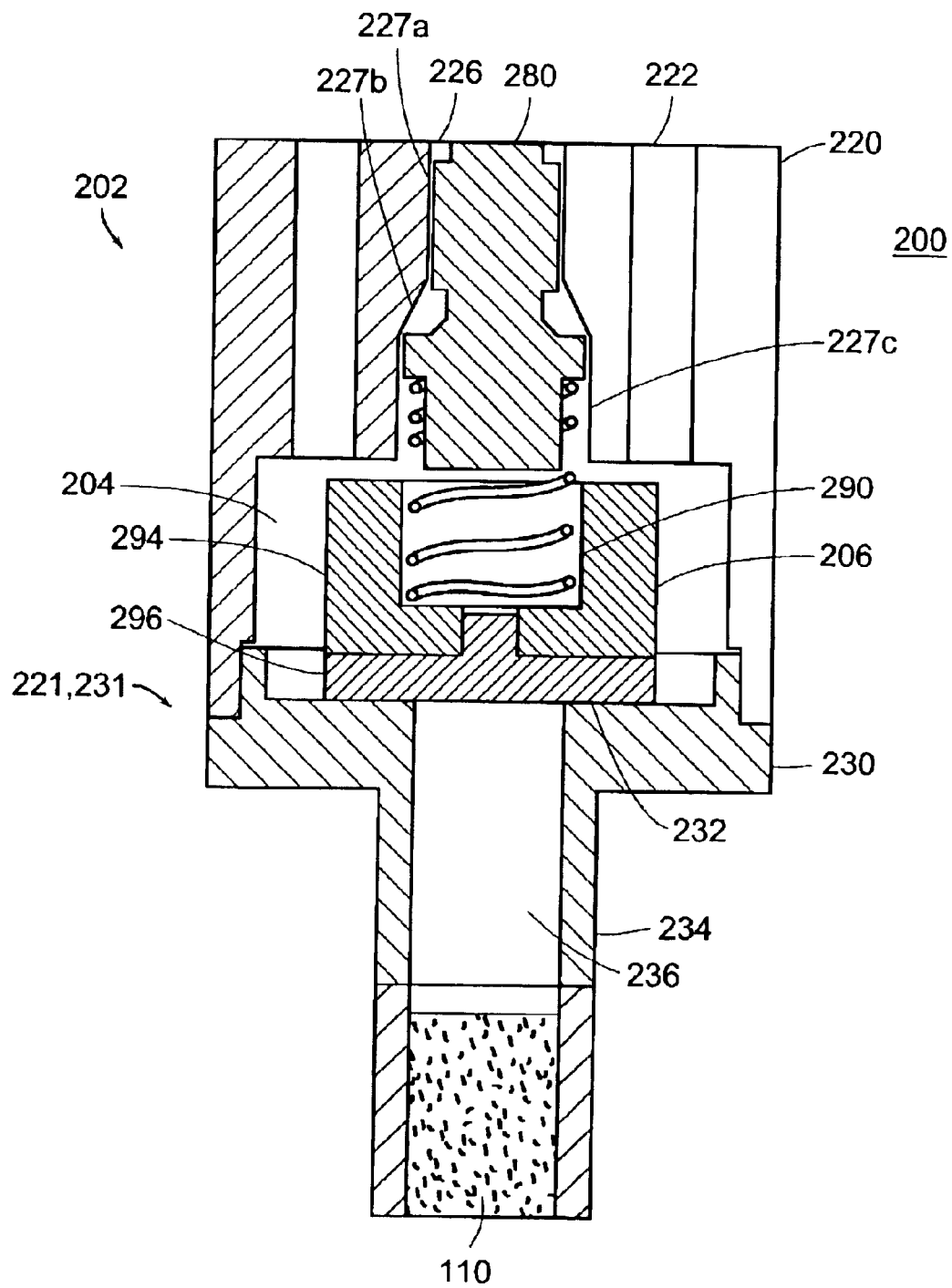
FIG. 7A is a cross-sectional side view of the automatic high negative pressure relief valve of FIG. 6 in the closed position.

The seating seal surface 232 is configured and arranged so as to cooperate with a portion of the seal subassembly 206 to form a fluid or pressure boundary between housing interior compartment 204 and the bottom cap through aperture 236, when the valve is in the closed position as shown in FIG. 7A. In the illustrative exemplary embodiment, the seating seal surface 232 is substantially flat, however, this is not particularly limiting as the seating seal surface can have any of a number of shapes and configurations known to those skilled in that art that cooperate with seal assembly 206 to form a fluid/pressure boundary or seal. It also is within the scope of the present invention to configure the seating seal surface 232 and the seal assembly 206 so that there is essentially line or edge sealing contact there between. The formation of the fluid/pressure boundary is described further below.

The seal assembly 206 is configured and arranged with a pocket 290 and a seating surface 292 that complements the bottom cap seating seal surface 232. As shown in FIGS. 7A,B the spring 108 is received in the pocket 290 and another end of the spring rests upon or is supported by the bottom of the pocket. As such, the pocket 290 is generally sized to receive the spring 108 therein and so the spring does not generally deflect or move laterally as the spring is compressed. In addition, the bottom of the pocket is sized and configured so said another one end of the spring is in mechanical engagement with the seal subassembly 206 as shown in FIG. 7A. Such mechanical engagement is one part of the mechanism by which the seal subassembly 206 is put into sealing engagement with the bottom cap seating seal surface 232.

In addition, the top and bottom caps 220, 230 are configured so a long axis of the top cap adjustment aperture 226 is generally aligned with a long axis of the seal assembly pocket 290. This provides a mechanism by which the spring 108 or other biasing mechanism is generally aligned within the housing 202 so that the force generated by the differential pressure developed across the seal subassembly 206 should act along a long axis of the spring. In this way, the force being generated by the differential pressure should generally cause the spring 108 to compress or relax.

When the top and bottom caps 220, 230 are secured together to form the housing 202, the spring 108 is compressed between the top and bottom caps a predetermined amount. The amount of compression and other characteristics of the spring 108 establish a preset differential pressure set point(s) for opening and closing the relief valve 200. As herein described, when the differential pressure is below the set point the spring force keeps the relief valve 200 in a closed condition and when the differential pressure exceeds the set point (i.e., the pressure with the chest drainage unit becomes more negative), the relief valve opens causing the spring to be compressed further. As the pressure within the chest drainage unit 300 is reduced to normal operating conditions, the spring relaxes and returns the relief valve 200 to the closed position.

In a particular embodiment, the seal assembly 206 includes first and second members 294, 296. The first member 294 is a rigid body that includes the pocket 290. The second member 296 is mechanically coupled to the first member 294 so the first and second members move as a unitary structure. A portion of the second member 296 is particularly configured so as to form the seating surface that mates with the bottom cap seating seal surface 232 to form the fluid/pressure boundary. In a further embodiment, the second member 296 is made from a soft elastomer material or any of a number of other materials known to those skilled in the art having a shore durometer from about 20 to 50, more particularly a shore durometer of about 30 to 40, to facilitate the formation of the fluid/pressure boundary/seal between the seal assembly 206 and the bottom cap seating seal surface 232. In a more specific embodiment, the valve seat seal member 138 further includes a coating, such as silicone fluid, to lubricate the valve seat and also to further facilitate the formation of a fluid/pressure boundary with the sealing subassembly 106.

Figure 7B:
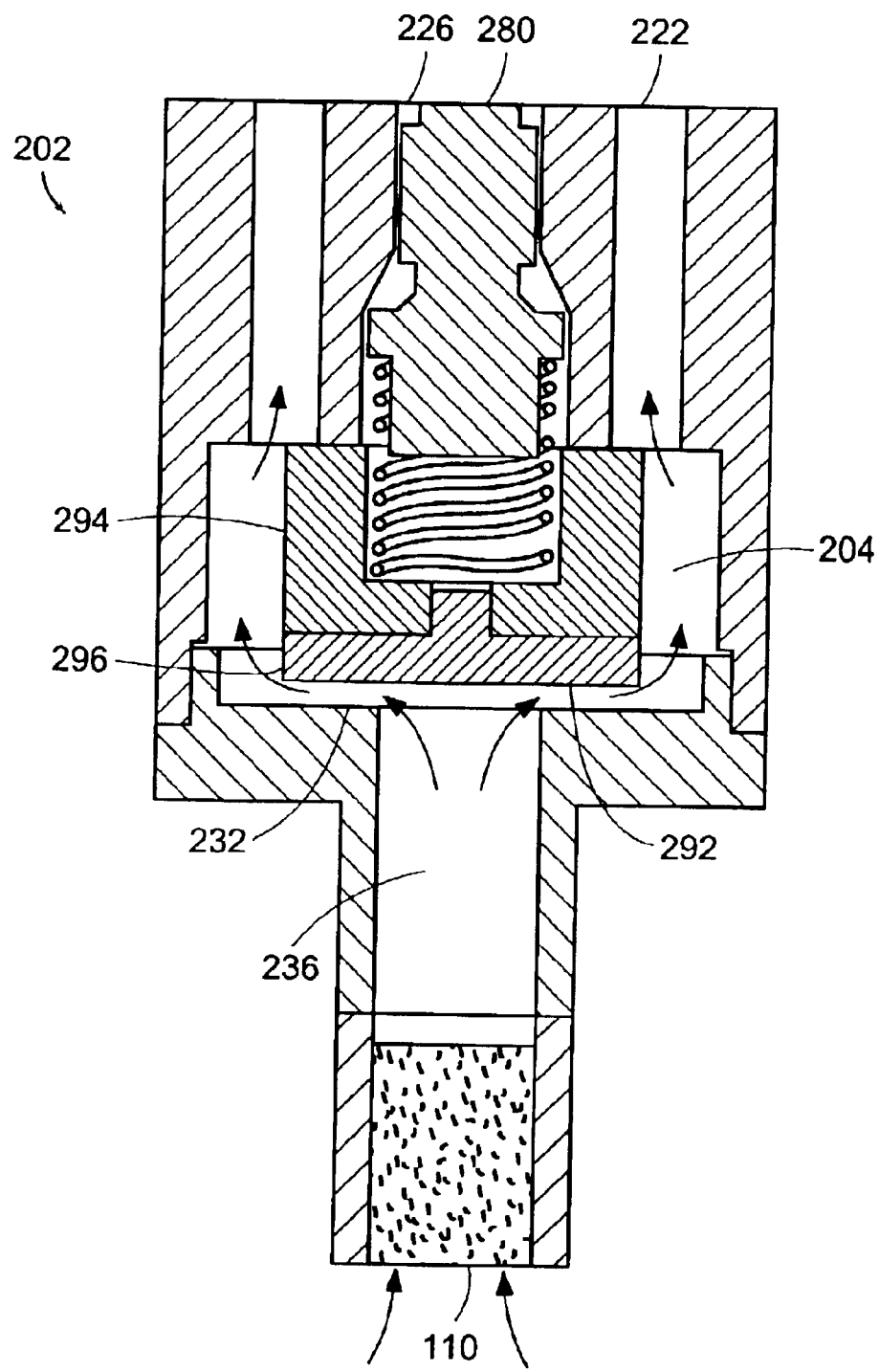
FIG. 7B is a cross-sectional side view of the automatic high-negative pressure relief valve of FIG. 6 in the open position.

The operation of an automatic high-negative pressure relief valve 200 can be best understood from the following discussion with reference to FIGS. 6–7, in particular FIGS. 7A,B. When the automatic high-negative pressure relief valve 200 is in the closed position, as illustrated in FIG. 7A, the seating surface of the seal assembly 206 is put into sealing engagement with the seating seal surface 232 of the bottom cap 230. This generally corresponds to the case where the suction pressure applied within the chest drainage unit collection chamber 306 is at or below (i.e., less negative) the predetermined suction pressure. Conversely, when the automatic high-negative pressure relief valve 200 is put in the open position, as illustrated in FIG. 7B, the seal assembly 206 moves away from the seating seal surface 232 of the bottom cap 230. This generally corresponds to the case where the suction pressure being imposed is greater than the predetermined suction pressure (i.e., pressure is more negative).

When the automatic high-negative pressure relief valve 200 is put into the open position the housing interior compartment 204 is put into fluid communication with the bottom cap through aperture 236. Thus, each of the top cap through apertures 222 also are fluidly coupled to the bottom cap through aperture 236 so that atmospheric air or gas from the gas source flows through the relief valve 200 and is admitted into the interior of the vessel having over pressure protection, such as the interior volume 310 of a chest drainage unit 300 so as to reduce the suction pressure or degree of vacuum being developed within the chest drainage device and more specifically the collection chamber 306 thereof. As indicated above, the selectively pre-compressed coil spring 108 provides a mechanism by which a portion of the seal subassembly 206 (e.g., the second member 296) is placed into sealing engagement with the bottom cap seating seal surface 232 or is moved away or spaced therefrom when the actual suction pressure exceeds the selected or predetermined suction pressure.

As indicated above, the automatic high-negative pressure relief valves 100, 200 according to the present invention are configurable such that the relief valve is fluidly coupled to atmosphere directly or via a filter element 110. The filter element comprises any of a number of materials known to those skilled in the art that acts like a bacterial filter so as to filter the incoming air so as to further reduce the potential for potential contaminates reaching the patient. Such materials are in the form of, for example, porous membranes or membrane filters as is known in the art and such materials include, for example, polypropylene or polytetrafluoroethylene (PTFE). In an illustrative embodiment, the filter element 110 is configured with openings of about 0.4 micron.

As indicated above, any of the automatic high-negative pressure valves of the present invention are particularly suited for use with what is commonly referred to as a chest drainage unit having either dry or wet suction control and/or a wet or dry patient seal. Referring now to FIGS. 9 and 10, there is shown an exemplary chest drainage unit 300 including a suction control 302, a patient seal 304, a collection chamber 306 and an automatic high-negative pressure relief valve 100 according to the present invention. Reference should be made to U.S. Ser. No. 09/336,471 (allowed) for further details regarding the chest drainage unit illustrated and referred to herein, the teachings of which are incorporated in their entirety herein.

The automatic high-negative pressure relief valve 100 is disposed within the chest drainage unit 300 so as to be fluidly coupled with the collection chamber 306. Some exemplary techniques for mounting the automatic high-negative pressure relief valve 100 to the chest drainage unit housing 308 such that the top cap through apertures 122 are in fluid communication with the interior 310 of the chest drainage unit housing are illustrated in FIGS. 8A, B. Although the automatic high-negative pressure relief valve 100 according to the first aspect of the present invention is illustrated in FIGS. 9–10, it should be recognized that any automatic high-negative pressure relief valve according to the present invention can be used in combination with any of a number of chest drainage units known to those skilled in the art.

When chest drainage units (CDU) where initially conceived as a mechanism to replace the well known three-bottle system, the CDU was constructed so that a fluid such as water was used to control the suction pressure being developed within the CDU effluent collection chamber and a fluid such as water was used to form a seal between the collection chamber and atmosphere, the patient seal. Subsequently, a number of devices were developed that did not involve the use of a fluid to control the suction pressure being developed, the so-called dry suction control devices. Further, a number of devices were developed that did not involve the use of a fluid to form the patient seal, the so-called dry patient seal devices.

Some exemplary chest drainage units that have a waterless or dry suction pressure regulation means and a dry or waterless patient seal include the PLEUR-EVAC Sahara series made by Genzyme Biosurgery and including those systems and/or devices described and disclosed in U.S. Pat. Nos. 4,738,671; 4,715,856; 4,554,370; and 4,747,844; 5,989,234, 6,368,311 and U.S. Ser. No. 09/336,471 (allowed) the teachings of which are incorporated herein by reference. Some exemplary chest drainage units that employ a waterless or dry suction pressure regulation means and a wet patient seal include a device and system such as the PLEUR-EVAC A-6000 series Adult/Pediatric Chest Drainage and Autotransfusion Systems made by Genzyme Biosurgery and including those systems and/or devices described and disclosed in U.S. Pat. Nos. 4,695,060; 4,105, 031; 4,784,642; 4,756,501; 4,443,220; 4,955,873; 4,955, 374; and 4,889,531, the teachings of which are incorporated herein by reference.

Although a preferred embodiment of the invention has been described using specific terms, such description is for illustrative purposes only, and it is to be understood that changes and variations may be made without departing from the spirit or scope of the following claims.

What is claimed is:

1. An automatic high negative pressure relief valve a portion of which is in fluid communication with a chamber, said relief valve comprising:

a housing having an interior compartment;

a biasing mechanism, a sealing member moveably disposed within the housing and being operably coupled to the biasing mechanism, wherein the sealing member includes a through aperture therein; and wherein the sealing member includes a flexible member that extends between interior surfaces of the housing dividing the interior compartment into first and second sub compartments, where the first sub compartment is fluidly coupled to the chamber and the second sub compartment is fluidly coupled to a gas source;

wherein the biasing member urges the sealing member against a seating surface to close the relief valve when the differential pressure developed across the sealing member is less than a predetermined value, wherein the seating surface comprises a conically shaped member and wherein the end of the through aperture sealingly engages the conically shaped member; and wherein the sealing member moves away from the seating surface to open the relief valve and to fluidly couple the chamber to the gas source when the differential pressure developed across the sealing member is less than a predetermined value.

2. The automatic high negative pressure relief valve of claim 1, wherein the biasing mechanism is one of a spring, a wave washer, a diaphragm, leaf spring, hydraulic member and a pneumatic piston.

3. The automatic high negative pressure relief valve of claim 1, wherein the flexible member is configured so as to not impose a changing force on the sealing member as the sealing member moves responsive to the differential pressure developed across the sealing member.

4. The automatic high negative pressure relief valve of claim 2, wherein the biasing mechanism further includes an adjusting mechanism operably coupled to the spring so as to adjust the amount of compression of the spring.

5. The automatic high negative pressure relief valve of claim 1, wherein the sealing member and the seating surface are configured and arranged so that they are in line contact with each other when the valve is in the closed position.

6. The automatic high negative pressure relief valve of claim 1, wherein the sealing member includes a through aperture therein, and wherein an end of the through aperture is sealingly engaged with the seating surface when the valve is closed and is spaced from the seating surface when the valve is opened, whereby the chamber and the gas source are fluidly coupled to each other via the through aperture.

7. The automatic high negative pressure relief valve of claim 6, wherein the seating surface is configured so the end of the through aperture sealingly engages the seating surface in edge contact when the valve is closed.

8. The automatic high negative pressure relief valve of claim 1, wherein the end of the through aperture and the conically shaped member are configured and arranged so that they are in line contact with each other when the valve is in the closed position.

9. The automatic high negative pressure relief valve of claim 1, wherein the conically shaped member contacts an interior surface of the through aperture and so that the interior surface and the conically shaped member are in line contact with each other when the valve is in the closed position.

10. The automatic high negative pressure relief valve of claim 1, further comprising an adjustment mechanism operably coupled to the biasing mechanism, the adjusting mechanism being configured and arranged so as to selectively adjust a force developed by the biasing mechanism corresponding to a set point of the relief valve.

11. An automatic high negative pressure relief valve a portion of which is in fluid communication with a chamber, said relief valve comprising:

a housing having an interior compartment and a seating surface;

a biasing mechanism, a sealing member moveably disposed within the housing including a floating seal member and a flexible member being mechanically coupled to each other;

wherein the floating seal member is operably coupled to the biasing mechanism and includes a through aperture therein;

wherein the flexible member extends between interior surfaces of the housing dividing the interior compartment into first and second sub compartments, where the first sub compartment is fluidly coupled to the chamber and the second sub-compartment is fluidly coupled to the gas source;

wherein an end of the floating seal member through aperture is moved against the seating surface so as to sealingly engage the end with the seating surface, when a differential pressure developed across the sealing member is less than a predetermined value and wherein the seating surface comprises a conically shaped member and wherein the end of the floating seal member through aperture sealingly engages the conically shaped member;

wherein the sealing member moves away from the seating surface to fluidly couple the chamber to the gas source via the floating seal member though aperture when the differential pressure developed across the sealing member is less than a predetermined value; and wherein the seating surface is configured so the end of the floating seal member through aperture sealingly engages the seating surface in edge contact when the valve is closed.

12. The automatic high negative pressure relief valve of claim 11, wherein the flexible member is configured so as to not impose a changing force on the sealing member as the sealing member moves responsive to the differential pressure developed across the sealing member.

13. The automatic high negative pressure relief valve of claim 11, wherein the conically shaped member contacts an interior surface of the floating seal member through aperture and so that the interior surface and the conically shaped member are in line contact with each other when the valve is in a closed position.

14. The automatic high negative pressure relief valve of claim 11, further comprising an adjustment mechanism operably coupled to the biasing mechanism, the adjusting mechanism being configured and arranged so as to selectively adjust a force developed by the biasing mechanism corresponding to a set point of the relief valve.

15. An automatic high negative pressure relief valve a portion of which is in fluid communication with a chamber, said relief valve comprising:

a housing having an interior compartment and a seating surface comprising a conical shaped member;

a spring, a sealing member moveably disposed within the housing including a floating seal member and a flexible member being mechanically coupled to each other;

wherein the floating seal member is operably coupled to the spring and includes a through aperture therein; wherein the flexible member extends between interior surfaces of the housing and the floating seal member thereby dividing the interior compartment into first and second sub compartments, where the first sub compartment is fluidly coupled to the chamber and the second sub compartment is fluidly coupled to the gas source;

wherein the flexible member is configured so as to not impose a changing force on the sealing member as the sealing member moves responsive to a differential pressure developed across the sealing member;

wherein an end of the floating seal member through aperture is moved against the seating surface conically shaped member by the spring when the differential pressure developed across the sealing member is less than a predetermined value so the seating surface conically shaped member contacts an interior surface of the floating seal member through aperture such that the interior surface and the conically shaped member are in one of edge or line contact with each other, thereby causing the end to sealingly engage the seating surface conically shaped member; and wherein the sealing member moves away from the seating surface conically shaped member to fluidly couple the first and second sub compartments via the floating seal member though aperture when the differential pressure developed across the sealing member is greater than a predetermined value, thereby also fluidly coupling the chamber and the gas source.

16. An automatic high negative pressure relief valve a portion of which is in fluid communication with a chamber, said relief valve comprising: a housing having an interior compartment, a seating surface having a conically shaped member and an aperture in the seating surface, wherein one portion of the interior compartment is fluidly coupled to the chamber and the aperture in the seating surface is fluidly coupled to a gas source such as atmosphere; a biasing mechanism, a sealing member moveably disposed within the housing interior compartment including a first and as second part that are mechanically coupled to each other;

wherein the sealing member first part is operably coupled to the biasing mechanism and responsive to differential pressure developed across the sealing member;

wherein the sealing member second part is configured and arranged so as to form a pressure boundary with the housing seating surface;

wherein the biasing member urges the sealing member second part against the conically shaped member of the seating surface to seal the housing through aperture and thereby close the relief valve when the differential pressure developed across the sealing member is less than a predetermined value; and wherein the sealing member moves away from the conically shaped member of the seating surface to un seal the housing through and thereby fluidly couple the chamber to the gas source when the differential pressure developed across the sealing member is greater than a predetermined value.

17. The automatic high negative pressure relief valve of claim 16,
wherein the material comprising the sealing member second part is formed of a soft material having a shore durometer in the range of from about 20 to 50.

18. The automatic high negative pressure relief valve of claim 16, further comprising an adjusting mechanism operably coupled to the biasing mechanism the adjusting mechanism being configured and arranged so as to selectively adjust a force developed by the biasing mechanism corresponding to a set point of the relief valve.

19. An apparatus for draining a fluid from a body comprising a collection chamber maintained under a negative pressure condition and an automatic high pressure negative relief, said automatic high negative pressure relief valve including:

a housing having an interior compartment;

a biasing mechanism, a sealing member moveably disposed within the housing and being operably coupled to the biasing mechanism;

wherein the sealing member includes a flexible member that extends between interior surfaces of the housing dividing the interior compartment into first and second sub compartments, where the first sub compartment is fluidly coupled to the collection chamber and the second sub compartment is fluidly coupled to a gas source;

wherein the biasing member urges the sealing member against a seating surface having a conically shaped member to close the relief valve when the differential pressure developed across the sealing member is less than a predetermined value; and wherein the sealing member moves away from the conically shaped member of the seating surface to open the relief valve and to fluidly couple the collection chamber to the gas source when the differential pressure developed across the sealing member is greater than a predetermined value.

20. An apparatus for draining a fluid from a body comprising a collection chamber maintained under a negative pressure condition and an automatic high pressure negative relief, said automatic high negative pressure relief valve including:

a housing having an interior compartment and a seating surface having a conically shaped member;

a biasing mechanism, a sealing member moveably disposed within the housing including a floating seal member and a flexible member being mechanically coupled to each other;

wherein the floating seal member is operably coupled to the biasing mechanism and includes a through aperture therein;

wherein the flexible member that extends between interior surfaces of the housing dividing the interior compartment into first and second sub compartments, where the first sub compartment is fluidly coupled to the collection chamber and the second sub compartment is fluidly coupled to a gas source;

wherein an end of the floating seal member through aperture is moved against the conically shaped member of the seating surface so as to sealingly engage the end with the conically shaped member of the seating surface when a differential pressure developed across the sealing member is less than a predetermined value;

wherein the sealing member moves away from the conically shaped member of the seating surface to fluidly couple the chamber to the gas source via the floating seal member though aperture when the differential pressure developed across the sealing member is less than a predetermined value; and wherein the seating surface is configured so the end of the floating seal member through aperture sealingly engages the seating surface in edge contact when the valve is closed.

21. An apparatus for draining a fluid from a body comprising a collection chamber maintained under a negative pressure condition and an automatic high pressure negative relief, said automatic high negative pressure relief valve including:

a housing having an interior compartment, a seating surface having a conically shaped member and an aperture in the seating surface, wherein one portion of the interior compartment is fluidly coupled to the collection chamber and the aperture in the seating surface is fluidly coupled to a gas source such as atmosphere;

a biasing mechanism, a sealing member moveably disposed within the housing interior compartment including a first and as second part that are mechanically coupled to each other; wherein the sealing member first part is operably coupled to the biasing mechanism and responsive to differential pressure developed across the sealing member;

wherein the sealing member second part is configured and arranged so as to form a pressure boundary with the housing seating surface;

wherein the biasing member urges the sealing member second part against the conically shaped member of the seating surface to seal the housing through aperture and thereby close the relief valve when the differential pressure developed across the sealing member is less than a predetermined value; and wherein the sealing member moves away from the conically shaped member of the seating surface to un seal the housing through and thereby fluidly couple the chamber to the gas source when the differential pressure developed across the sealing member is greater than a predetermined value.

* * * * *